US007094803B2

(12) United States Patent
Killday et al.

(10) Patent No.: US 7,094,803 B2
(45) Date of Patent: Aug. 22, 2006

(54) BIOLOGICALLY ACTIVE RASPAILAMIDE COMPOUNDS

(75) Inventors: K. Brian Killday, Ft. Pierce, FL (US); Amy E. Wright, Fort Pierce, FL (US); Shirley A. Pomponi, Ft. Pierce, FL (US); Ross E. Longley, Tallahassee, FL (US)

(73) Assignee: Harbor Branch Oceanographic Institution, Inc., Fort Pierce, FL (US)

( * ) Notice: Subject to any disclaimer, the term of this patent is extended or adjusted under 35 U.S.C. 154(b) by 8 days.

(21) Appl. No.: 10/889,925

(22) Filed: Jul. 12, 2004

(65) Prior Publication Data

US 2005/0038106 A1 Feb. 17, 2005

Related U.S. Application Data

(60) Provisional application No. 60/486,687, filed on Jul. 11, 2003.

(51) Int. Cl.
*A61K 31/35* (2006.01)

(52) U.S. Cl. ....................................... 514/459; 549/415

(58) Field of Classification Search ................ 549/415; 514/459

See application file for complete search history.

(56) References Cited

OTHER PUBLICATIONS

Mayer et al, Mini Review, Marine Pharmacology in 2000: Antitumor and cytotoxic compounds, Int. J. Cancer: 105,291-299 (2003).*

Barrand, M., Bagrij, T., and Neo, S. (1997)., General Pharmacology, 28 (5): 639-645.

Bellamy, W. T. (1996), Annu. Rev. Pharmacol. Toxicol., 36: 161-183.

Broxterman, H. J., Giaccone, G., and Lankelma, J. (1995), Current Opinion in Oncology, 7:532-540.

Casazza, A. M. and C. R. Fairchild (1996) "Paclitaxel (Taxol® ): mechanisms of resistance" *Cancer Treat Res.* 87:149-171.

Komorov, P. G., Shtil, A. A., Holian, O. Tee, L., Buckingham, L., Mechetner, E. B., Roninson, I. B., and Coon, J. S. (1998), Oncology Research, 10:185-192.

Krishan, A., Fitz, C. M., and Adritsch, I. (1997), Cytometry, 29:279-285.

Kruh, G. D., Gaughan, K. T., Goodwin, A., and Chan, A. (1995), Journal of the National Cancer Institute, 87 (16):1256-1258.

Miller, D. W., Fontain, M., Kolar, C., and Lawson, T. (1996). Cancer Letters, 107:301-306.

Sugawara, I. (1995) "Review: Multidrug resistance: role of Multidrug resistance-associated protein (MRP)" *The Cancer Journal* 8(2):59-61.

* cited by examiner

*Primary Examiner*—Amelia A. Owens
(74) *Attorney, Agent, or Firm*—Saliwanchik, Lloyd & Saliwanchik

(57) ABSTRACT

The subject invention provides novel compositions of biologically active polyketide compounds that can advantageously be used in blocking cellular proliferation and treatment of cancer.

12 Claims, 6 Drawing Sheets

ROE correlations

BIOLOGICALLY ACTIVE RASPAILAMIDE COMPOUNDS

CROSS-REFERENCE TO A RELATED APPLICATION

This application claims the benefit of U.S. provisional application Ser. No. 60/486,687, filed Jul. 11, 2003.

FIELD OF THE INVENTION

This invention relates to organic compounds and compositions which have useful therapeutic properties. More particularly, the invention concerns novel polyketide-derived compounds having anti-proliferative and antitumor activities, pharmaceutical compositions comprising such compounds, and methods of their use for therapeutic purposes.

BACKGROUND OF THE INVENTION

Of great importance to man is the control of pathological cellular proliferation such as that which occurs in the case of cancer. Considerable research and resources have been devoted to oncology and antitumor measures including chemotherapy. While certain methods and chemical compositions have been developed which aid in inhibiting, remitting, or controlling the growth of, for example, tumors, new methods and antitumor chemical compositions are needed. Anti-proliferative agents can also be useful in treating autoimmune diseases and inflammatory disease.

In searching for new biologically active compounds, it has been found that some natural products and organisms are potential sources for chemical molecules having useful biological activity of great diversity. For example, the diterpene commonly known as paclitaxel, isolated from several species of yew trees, is a mitotic spindle poison that stabilizes microtubules and inhibits their depolymerization to free tubulin (Fuchs, D. A., R. K. Johnson [1978*] Cancer Treat. Rep.* 62:1219–1222; Schiff, P. B., J. Fant, S. B. Horwitz [1979*] Nature* (London) 22:665–667). Paclitaxel is also known to have antitumor activity and has undergone a number of clinical trials which have shown it to be effective in the treatment of a wide range of cancers (Rowinski, E. K. R. C. Donehower [1995*] N. Engl. J. Med.* 332:1004–1014). See also, e.g., U.S. Pat. Nos. 5,157,049; 4,960,790; and 4,206,221.

Marine sponges have also proven to be a source of biologically active chemical molecules. A number of publications disclose organic compounds derived from marine sponges including Scheuer, P. J. (ed.) *Marine Natural Products, Chemical and Biological Perspectives*, Academic Press, New York, 1978–1983, Vol. I-V; Uemura, D., K. Takahashi, T. Yamamoto, C. Katayama, J. Tanaka, Y. Okumura, Y. Hirata (1985) *J. Am. Chem. Soc.* 107:4796–4798; Minale, L. et al. (1976) *Fortschr. Chem. org. Naturst.* 33:1–72 Faulkner, D. J., *Nat. Prod. Reports* 1984, 1, 251–551; ibid. 1987, 4, 539; ibid 1990, 7, 269; ibid 1993, 10, 497; ibid 1994, 11, 355; ibid 1995, 12, 22; ibid 1998, 15:113–58; ibid 2000 17:1–6; ibid 2000 17: 7–55; ibid 2001, 18: 1–49; 2002,19:1–48.; Gunasekera, S. P., M. Gunasekera, R. E. Longley and G. K. Schulte (1990) *J. Org. Chem.*, 55:4912–4915.; Horton, P.A., F.E. Koehn, R. E. Longley, and O. J. McConnell, (1994) *J. Am. Chem. Soc.* 116: 6015–6016.

The success of chemotherapy for the treatment of various cancers can be substantially negated though cellular mechanisms which have evolved to enable neoplastic cells to subvert the cytotoxic effects of the drug. Some cells have developed mechanisms, which confer resistance to a number of structurally unrelated drugs. This multi-drug resistance (or MDR) phenomenon may arise through a number of different mechanisms. One of these involves the ability of a cell to reduce intracellular concentrations of a given drug through efflux from cytoplasm through and out the cell membrane by a series of unique ATP-dependent transporter proteins called-P-glycoproteins (Pgp) (Casazza, A. M. and C. R. Fairchild [1996] "Paclitaxel (Taxol®): mechanisms of resistance" *Cancer Treat Res.* 87:149–171). The surface membrane, 170 kDa Pgp, is encoded by the mdr-1 gene and appears to require substrate binding before transport begins. A wide range of compounds. including a number of structurally unrelated chemotherapeutic agents (adriamycin, vinblastine, colchicine, etoposide and Taxol), are capable of being transported by Pgp and render the cell resistant to the cytotoxic effects of these compounds. While many normal cell types possess Pgp, in general, tumor cell lines, which possess high levels of mRNA specific for Pgp, also exhibit overexpression of membrane Pgp and demonstrate resistance to various drugs. This intrinsic resistance can be increased multifold by incubation of cells with stepwise increasing doses of a particular drug over a period of several months. This can be further facilitated by the addition of the MDR reversal agent, verapamil (Casazza, A. M. and C. R. Fairchild [1996] supra) in combination with the particular drug. Drug resistant cell lines produced in this fashion exhibit resistance to drug cytotoxicity from 20 to 500 fold, compared to parental cell lines.

An additional target for cancer drug discovery is a high molecular weight membrane protein associated with multidrug resistance properties of certain tumor cells known as the multidrug resistance-associated protein (MRP). MRP is a 190 kD membrane-bound glycoprotein (Bellamy, W. T. [1996], Annu. Rev. Pharmacol. Toxicol., 36: 161–183.) which belongs to the same family of proteins as the p-glycoprotein pump P-gp (Broxterman, H. J., Giaccone, G., and Lankelma, J. [1995], Current Opinion in Oncology, 7:532–540.) but shares less than 15% homology of amino acids with P-gp (Komorov, P. G., Shtil, A. A., Holian, O., Tee, L., Buckingham, L., Mechetner, E. B., Roninson, I. B., and Coon, J. S. [1998], Oncology Research, 10: 185–192.). MRP has been found to occur naturally in a number of normal tissues, including liver, adrenal, testis, and peripheral blood mononuclear cells (Krishan, A., Fitz, C. M., and Andritsch, I. [1997], Cytometry, 29: 279–285). MRP has also been identified in tissues of the lung, kidney, colon, thyroid, urinary bladder, stomach, spleen (Sugawara, I. [1998] The Cancer Journal, 8(2) and skeletal muscle (Kruh, G. D., Gaughan, K. T., Godwin, A., and Chan, A. [1995], Journal of the National Cancer Institute, 87(16): 1256–1258.). High levels of MRP have been implicated in multidrug resistance (MDR) in cancers of the lung and pancreas (Miller, D. W., Fontain, M., Kolar, C., and Lawson, T. [1996]. Cancer Letters, 107: 301–306.), and in neuroblastomas, leukemias and cancer of the thyroid (Kruh, G. D., Gaughan, K. T., Godwin, A., and Chan, A. [1995], Journal of the National Cancer Institute, 87(16): 1256–1258.), as well as bladder, ovarian and breast cancers (Barrand, M., Bagrij, T., and Neo, S. [1997]., General Pharmacology, 28(5): 639–645.). MRP-mediated MDR involves some of the same classes of compounds as those which are mediated by P-gp, including vinca alkaloids, epipodophyllotoxins, anthracyclins and actinomycin D (Barrand, M., Bagrij, T., and Neo, S. [1997]., General Pharmacology, 28(5): 639–645). However, the substrate specificity has been demonstrated to differ from that of P-gp (Komorov, P. G., Shtil, A. A., Holian, O., Tee, L., Buckingham, L., Mechetner, E. B., Roninson, I. B., and Coon, J. S. [1998], Oncology Research, 10: 185–192.). Drugs which would inhibit or which are not substrates for the MDR pump would, therefore, be useful as chemotherapeutic agents.

BRIEF SUMMARY OF THE INVENTION

The subject invention provides novel compositions of biologically active compounds that have utility for use in inhibiting cellular proliferation. In a specific embodiment, the compounds and compositions of the subject invention can be used in the treatment of cancer.

In one embodiment, the novel compositions and methods of the subject invention can be used in the treatment of an animal hosting cancer cells including, for example, inhibiting the growth of tumor cells in a mammalian host. More particularly, the subject compounds can be used for inhibiting in a human the growth of tumor cells, including cells of breast, colon, CNS, ovarian, renal, prostate, liver, pancreatic, uterine, or lung tumors, as well as human leukemia or melanoma cells. The mechanisms for achieving anticancer activity exhibited by the subject compounds would lead a person of ordinary skill in the art to recognize the applicability of the subject compounds, compositions, and methods to additional types of cancer as described herein.

In accordance with the subject invention, methods for inhibiting cancer cells in a host include contacting tumor cells with an effective amount of the new pharmaceutical compositions of the invention. The cancer cells inhibited by the invention are those which are susceptible to the subject compounds described herein or compositions comprising those compounds.

In specific embodiments, the subject invention provides new polyketides, as exemplified by Raspailamide A (I) and Raspailamide B (II). The raspailamides have not been isolated previously from a natural source nor have they been previously synthesized.

(I)

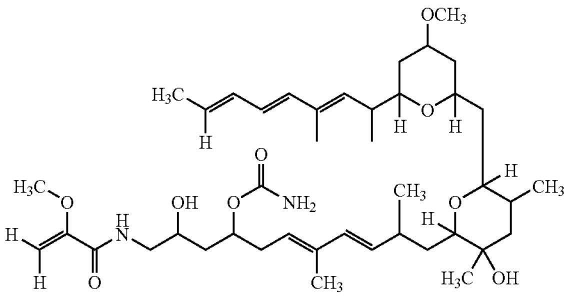

-continued (II)

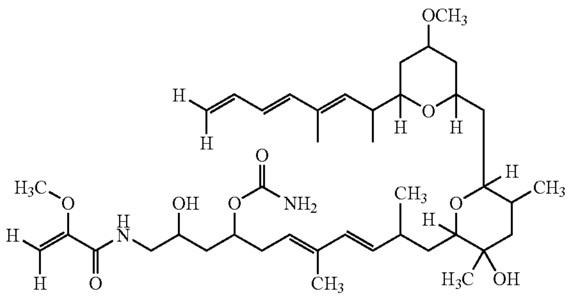

Additional aspects of the invention include the provision of methods for producing the new compounds and compositions.

Other objects and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

BRIEF SUMMARY OF THE FIGURES

The file of this patent contains at least one drawing executed in color. Copies of this patent with color drawings (s) will be provided by the Patent and Trademark Office upon request and payment of the necessary fee.

DETAILED DISCLOSURE OF THE INVENTION

Figure 1:
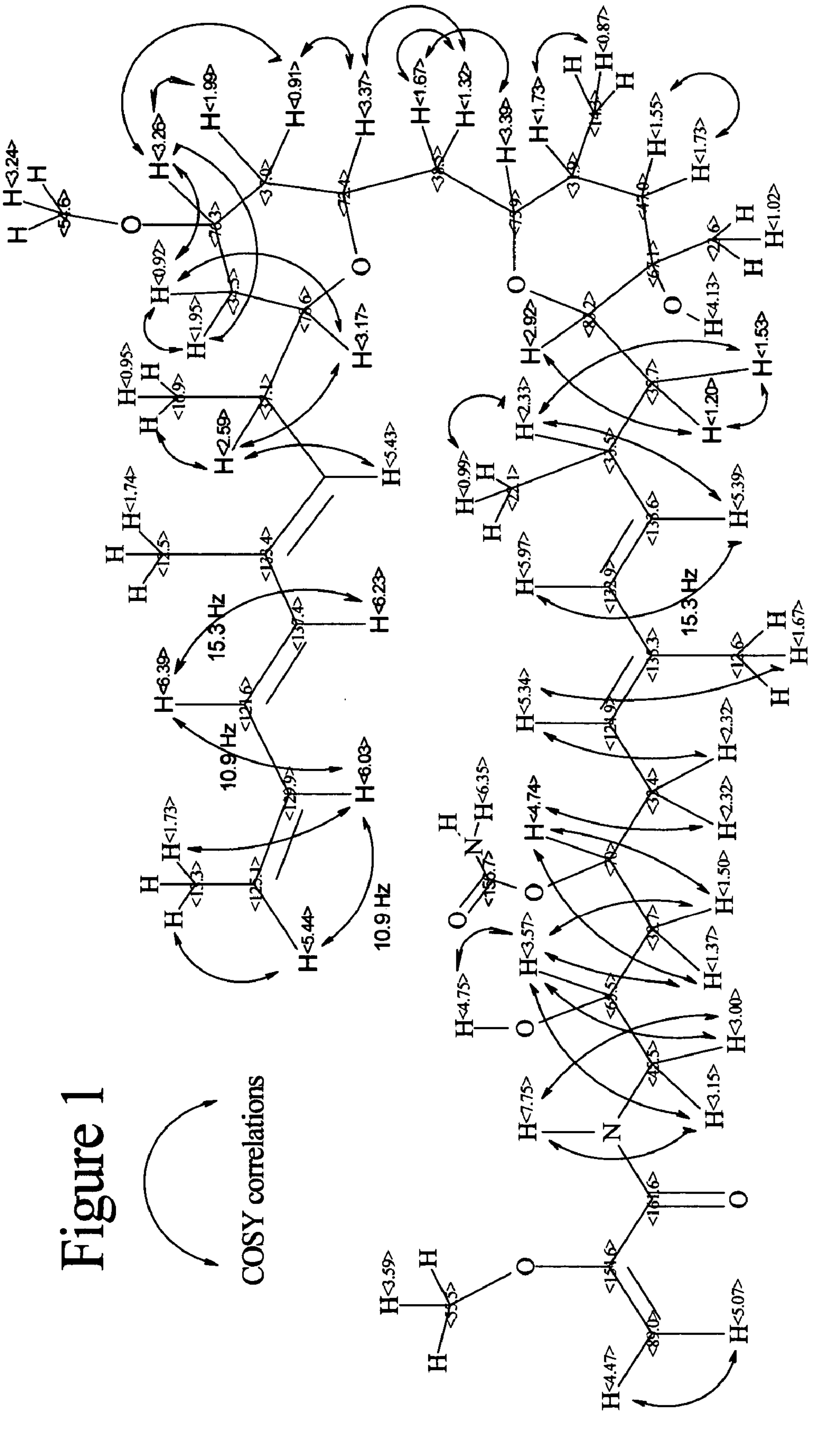
FIG. 1 shows $^{1}H$-$^{1}H$ scalar couplings determined using DQF-PSCOSY and TOCSY data.

The subject invention provides novel compositions of biologically active polyketide compounds which are useful for inhibiting pathological cellular proliferation.

Advantageously the polyketide compounds of the subject invention can be used to inhibit unwanted cellular proliferation, including the pathogenic proliferation of tumor cells.

In a preferred embodiment, these compounds can be used for treating cancer. More specifically, the novel compounds, compositions and methods of use can advantageously be used to inhibit the growth of tumor and other cancer cells in a mammalian host. As described herein, the compounds of the subject invention have utility for use in the treatment of cancer. More particularly, the subject compounds can be used for inhibiting in a human the growth of tumor cells, including cells of breast, prostate, colon, CNS, ovarian, renal, liver, pancreatic, uterine, or lung tumors, as well as human leukemia or melanoma cells. The compounds also have utility in the treatment of multi-drug resistant cancer cells.

In a preferred embodiment, the subject invention provides compounds having the following formulas:

(I)

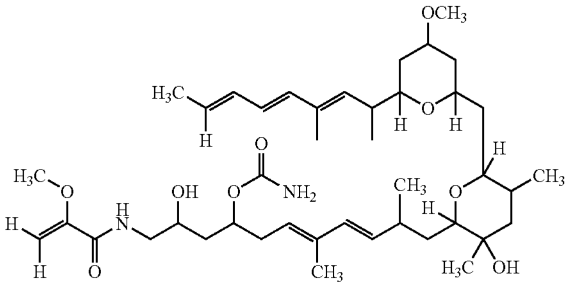

and (II)

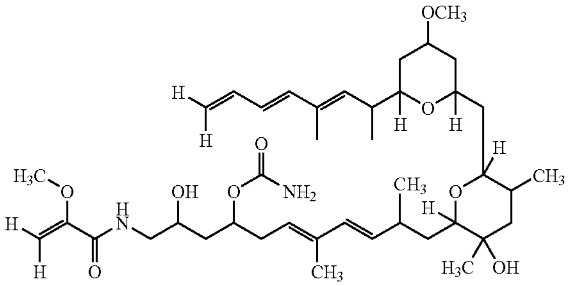

The subject invention further pertains to isolated enantiomeric compounds. The isolated enantiomeric forms of the compounds of the invention are substantially free from one another (i.e. in enantiomeric excess). In other words, the "R" forms of the compounds are substantially free from the "S" forms of the compounds and are, thus, in enantiomeric excess of the "S" forms. Conversely "S" forms of the compounds are substantially free of the "R" forms of the compounds and are, thus, in enantiomeric excess of the "R" forms. In one embodiment of the invention, the isolated enantiomeric compounds are at least about in 80% enantiomeric excess. In a preferred embodiment, the compounds are in at least about 90% enantiomeric excess. In a more preferred embodiment, the compounds are in at least about 95% in enantiomeric excess. In a more preferred embodiment, the compounds are in at least about 97.5% enantiomeric excess. In a most preferred embodiment, the compounds are in at least about 99% enantiomeric excess.

In accordance with the subject invention, methods for inhibiting cancer in a host include contacting cancer cells with an effective amount of the new pharmaceutical compositions of the invention. The tumor cells inhibited by the invention are those which are susceptible to the subject compounds described herein or compositions comprising those compounds.

The subject invention further provides methods of use of the new compounds and compositions of the invention, e.g., methods of inhibiting tumors and other cancer cells in an animal, preferably a mammal. Most preferably, the invention comprises a method for the antitumor treatment of a human in need of such treatment, i.e., a human hosting cancer cells, including breast, colon, liver, pancreatic, uterine, or lung tumor cells, or leukemia cells including multi-drug resistant cancer cells.

In preferred embodiments of the invention, the compounds are substantially pure, i.e., contain at least 95% of the compound as determined by established analytical methods.

In further preferred methods of the invention, salts within the scope of the invention are made by adding mineral acids, e.g., HCl, $H_2SO_4$, or strong organic acids, e.g., formic, oxalic, in appropriate amounts to form the acid addition salt of the parent compound or its derivative. Also, synthesis type reactions may be used pursuant to known procedures to add or modify various groups in the preferred compounds to produce other compounds within the scope of the invention.

As used in this application, the terms "analogs," refers to compounds which are substantially the same as another compound but which may have been modified by, for example, adding or removing side groups.

The scope of the invention is not limited by the specific examples and suggested procedures and uses related herein since modifications can be made within such scope from the information provided by this specification to those skilled in the art.

Materials and Methods

Figure 2:
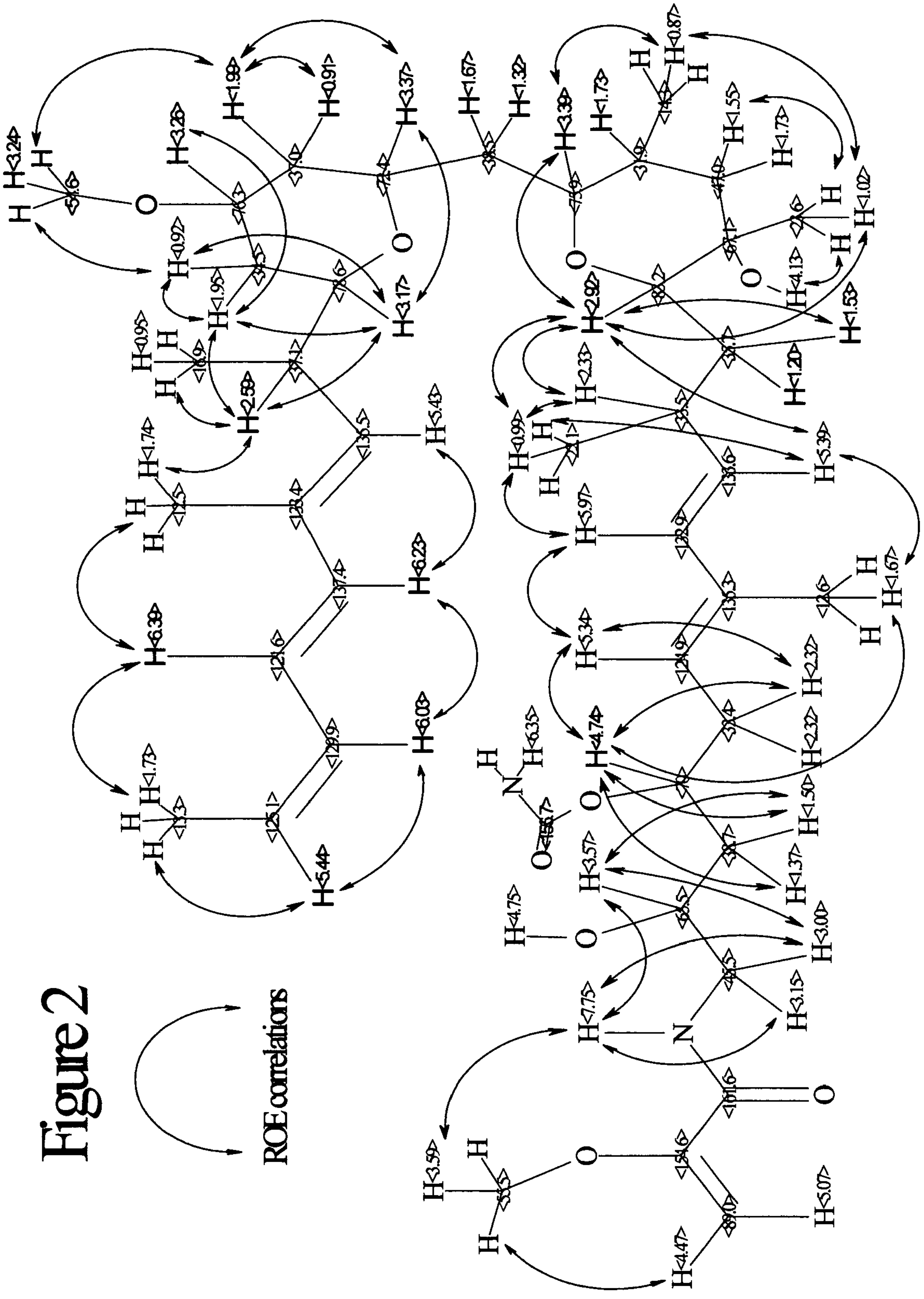
FIG. 2 shows the ROESY correlations and the cis/trans assignments of the olefinic bonds.
Figure 3:
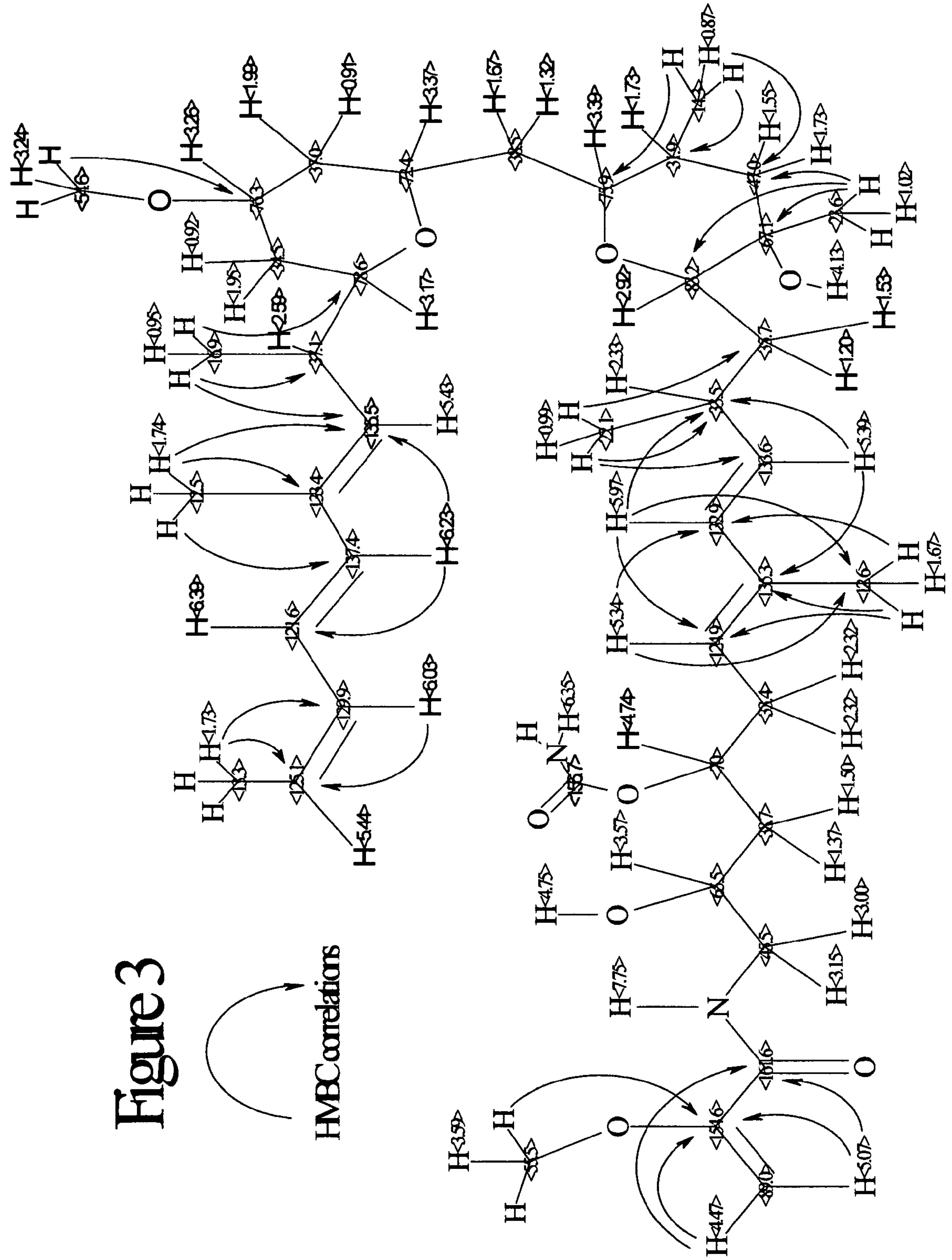
FIG. 3 shows one and multiple bond $^{1}H$-$^{13}C$ connectivities determined via the 2D proton detected HMQC, and HMBC experiments.
Figure 4:
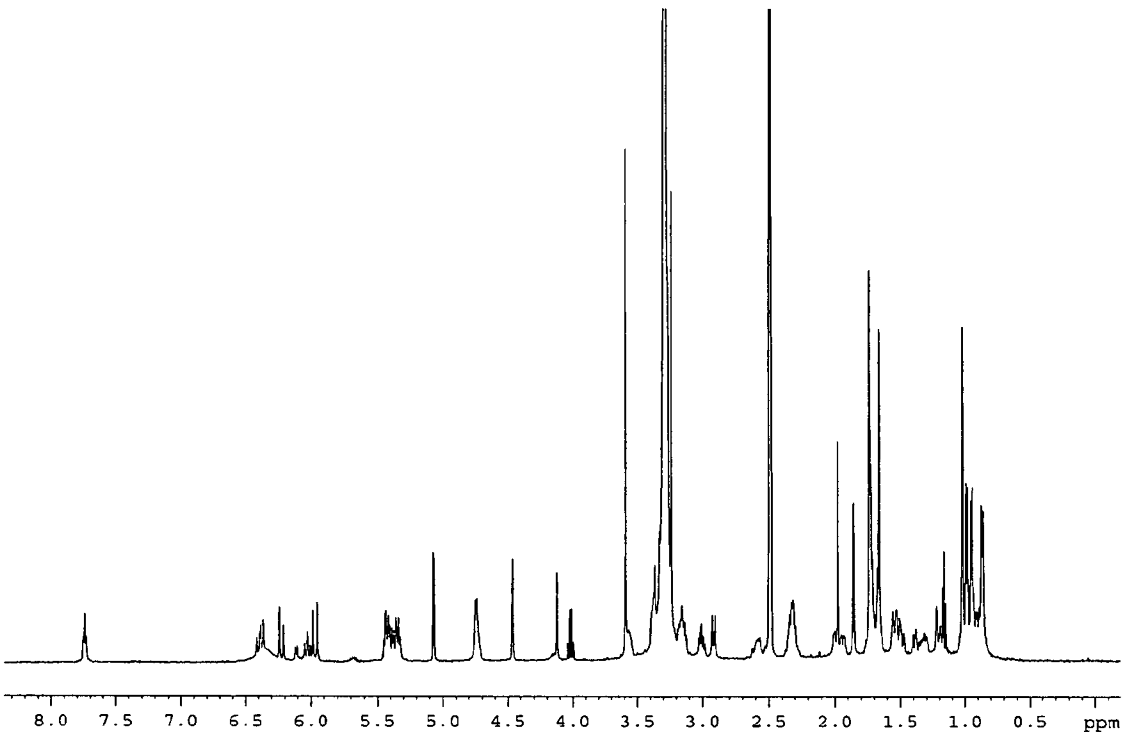
FIG. 4 shows $^{1}H$ NMR spectrum of Raspailamide A (I) in DMSO-$d_6$
Figure 5:
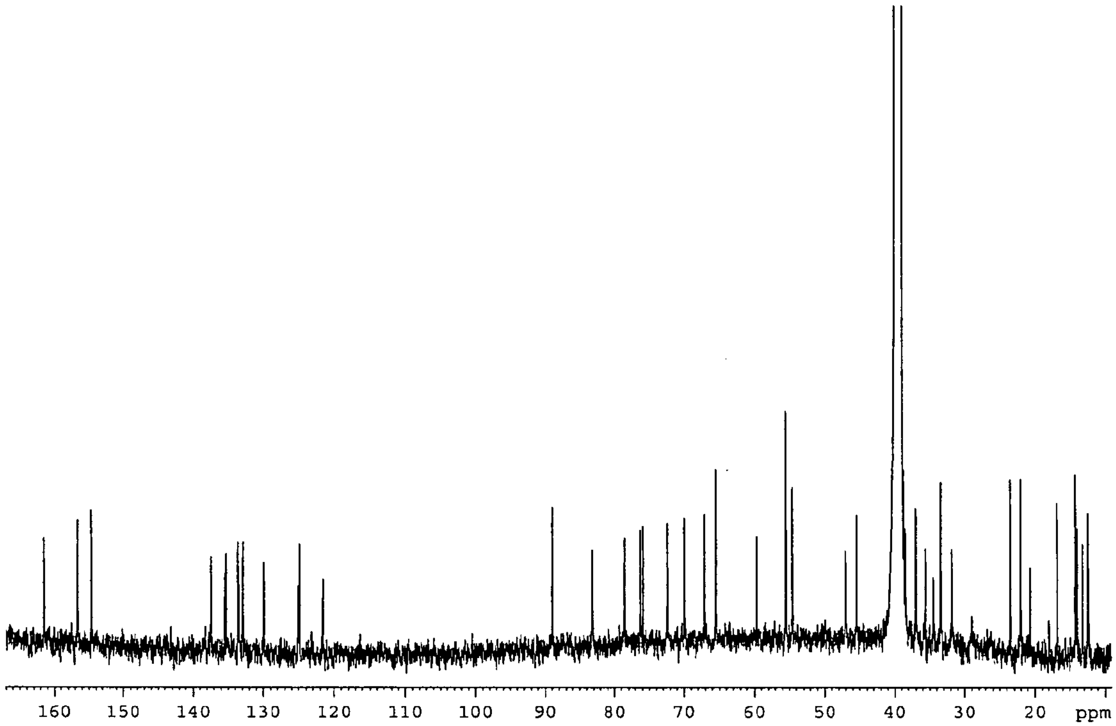
FIG. 5 shows $^{13}C$ NMR spectrum of Raspailamide A (I) in DMSO-$d_6$
Figure 6:
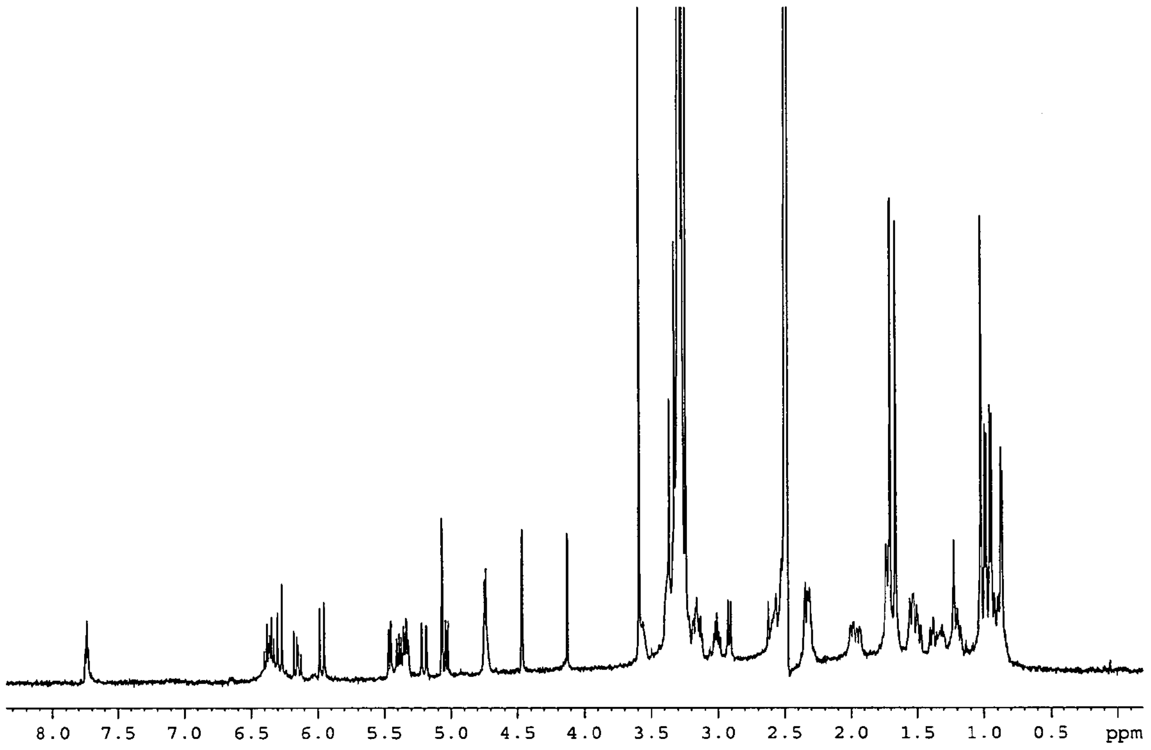
FIG. 6 shows $^{1}H$ NMR spectrum of Raspailamide B (II) in DMSO-$d_6$

The chemical structures of Raspailamides A (I) and B (II) were determined utilizing extensive NMR spectral analysis. The NMR and ESIMS spectra of (I) indicated a molecular formula of $C_{42}H_{68}N_2O_9$, with a hydrogen deficiency index of ten. The NMR spectral data indicated the presence of five olefinic bonds and two carbonyls. The APT formula ($C_{42}H_{63}$) indicated five of these protons not attached to carbon. The amide, carbamate, and alcohol protons (7.75, 6.35(2H), 4.75, and 4.13 respectively) were exchanged on addition of D20. $^1H$-$^1H$ scalar couplings (FIG. 1) were determined using DQF-PSCOSY and TOCSY data and the DISCO-TOCSY method (Killday, K. B. "Differences and Sums of Traces Within COSY and TOCSY Spectra; DISCO and DISCO-TOCSY," Presented at the 39th Annual Meeting of the American Society of Pharmacognosy, Orlando, Fla., 1998). The ROESY correlations (FIG. 2) support the cis/trans assignments of the olefinic bonds. NMR spectral data for the n-terminal methyl enol functionality compare favorably to those reported for the corresponding functionality of the esperamicins, potent antitumor antibiotics from *Actinomadura verrucosospora* (Konishi, M.; Ohkuma, H.; Saitoh, K.; Kawaguchi, H.; Golik, J.; Dubay, G.; Groenewold, G.; Krishnan, B.; Doyle, T. W. *J. Antibiotics.* 1985, 38, 1605–1609). One and multiple bond $^1H$-$^{13}C$ connectivities were determined via the 2D proton detected HMQC, and HMBC (FIG. 3) experiments.

Spectral data were measured on the following instruments: NMR, Bruker AMX-500 with 5 mm BBO probe; Flow Injection Electrospray Ionization Mass Spectroscopy (FI-EINS), Finnigan MATLCQ. $^1H$-NMR chemical shifts are reported as δ values in ppm relative to DMSO-$d^6$ (2.49 ppm). $^{13}$C-NMR chemical shifts are reported as δ values in ppm relative to DMSO-$d^6$ (39.5 ppm). 13C multiplicities were measured using the DEPT sequence. NOe correlations were determined via the PS-NOESY and PS-ROESY sequences.

A more complete understanding of the invention can be obtained by reference to the following specific examples of compounds, compositions, and methods of the invention. The following examples illustrate procedures for practicing the invention. These examples should not be construed as limiting. All percentages are by weight and all solvent mixture proportions are by volume unless otherwise noted. It will be apparent to those skilled in the art that the examples involve use of materials and reagents that are commercially available from known sources, e.g., chemical supply houses, so no details are given respecting them.

EXAMPLE 1

Isolation and Structure Elucidation of Raspailamides A (I) and B (II)

A. Collection and Taxonomy of the Source Organism

A sample of a sponge identified as belonging to the Family Raspailiidae (Phylum: Porifera, Class Demospongiae, Order Poecilosclerida, Family Raspailiidae) was collected using the Johnson Sea Link manned submersible at a depth of 81.7 m off the North Jamaican Coast (latitude 18 28.069'N, longitude77 21.579'W). The sponge morphology is spherical to lobate with a felt like surface and apical oscules. It is orange both externally and internally. A reference sample preserved in ethanol has been deposited in the Harbor Branch Oceanographic Museum (catalog number 003:01006, DBMR number 30-VEI-93-4-0 11) and is available for taxonomic evaluation by those skilled in the art.

B. Isolation and Structure Elucidation of Raspailamide A (I).

The specimen was stored frozen until extraction. The diced sponge (HBOI Sample number 30-VIII-93-4-011, 310 g) was extracted exhaustively by blending with ethanol in a blender (6×400 mL).

After filtration of the extract, the solvent was removed by distillation under reduced pressure to obtain an orange solid (12.1 g) which was partitioned between ethyl acetate and water.

The ethyl acetate partition (2.49 g) was subjected to VCC on a silica gel column (Kieselgel 60H) utilizing a step gradient from 40% to 100% ethyl acetate in heptane. The fraction eluting with 100% ethyl acetate was further purified via silica gel HPLC (Whatman Partisil 10, 250×10 mm, 100% ETOAc, 6 mL/min). Raspailamide A (I) (4.5 mg, 0.0015% of wet weight) eluted at a retention time of 7.2 min. A shoulder eluting at the end of the peak containing (I) was also collected.

Evaluation of the $^1$H NMR spectrum of this mixture showed it to contain a mixture of (I) and a closely related compound.

The mixture was further separated via reversed-phase HPLC (Whatman Partisil 10 ODS-3, 250×10 mm, MeOH/$H_2O$,80:20,4 mL/min) to yield Raspaliamide B (II) (0.3 mg, $9.7\times10^{-5}$% of wet weight) eluting with a retention time of 8.0 min along with additional raspailamide A (I) (0.9 mg) eluting with a retention time of 9.6 min.

TABLE 1

(I)

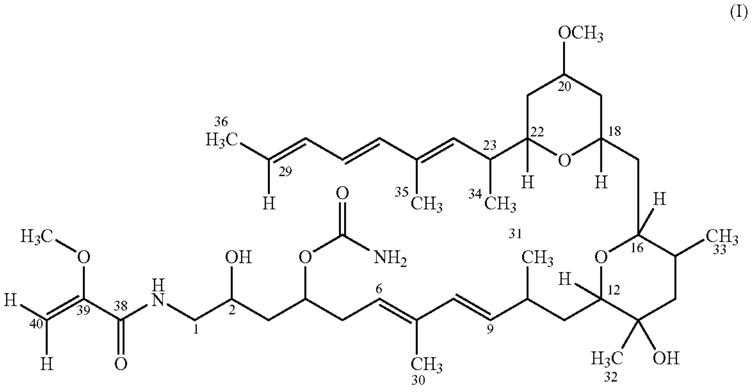

NMR Data for Raspailamide A (I) (DMSO-d6)

| Atom # | $^{13}$C δ mult. | $^1$H δ mult (J in Hz) |
|---|---|---|
| 1 | 45.5 t | 3.15 ddd |
| | | 3.00 ddd |
| 2 | 65.5 d | 3.57 m |
| 3 | 38.7 t | 1.50 dd |
| | | 1.37 dd |
| 4 | 70.0 d | 4.74 m |
| 5 | 33.4 t | 2.32 m, 2H |
| 6 | 124.9 d | 5.34 m |
| 7 | 135.3 s | — |
| 8 | 132.9 d | 5.97 d (16.1) |
| 9 | 133.6 d | 5.39 m |
| 10 | 33.5 d | 2.33 m |
| 11 | 35.7 t | 1.53 m |
| | | 1.20 m |
| 12 | 83.2 d | 2.92 m |
| 13 | 67.1 s | — |

TABLE 1-continued (I)

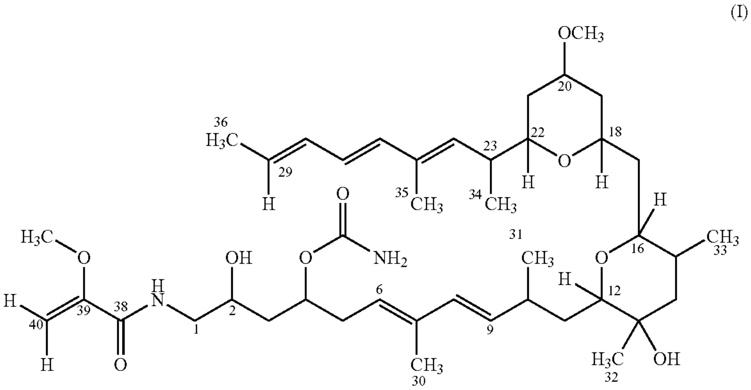

NMR Data for Raspailamide A (I) (DMSO-d6)

| Atom # | $^{13}C$ δ mult. | $^{1}H$ δ mult (J in Hz) |
|---|---|---|
| 14 | 47.0 t | 1.73 m<br>1.55 m |
| 15 | 31.9 d | 1.73 m |
| 16 | 75.9 d | 3.39 m |
| 17 | 38.5 t | 1.67 ddd<br>1.32 m |
| 18 | 72.4 d | 3.37 m |
| 19 | 37.0 t | 1.99 m<br>0.91 m |
| 20 | 76.3 d | 3.26 m |
| 21 | 34.5 t | 1.95 m<br>0.92 m |
| 22 | 78.6 d | 3.17 m |
| 23 | 37.1 d | 2.59 m |
| 24 | 135.5 d | 5.43 m |
| 25 | 133.4 s | — |
| 26 | 137.4 d | 6.23 d (15.3) |
| 27 | 121.6 d | 6.39 dd (15.3, 10.9) |
| 28 | 129.9 d | 6.03 m |
| 29 | 125.1 d | 5.44 dt |
| 30 | 12.6 q | 1.67 s, 3H |
| 31 | 22.1 q | 0.99 d, 3H (6.8) |
| 32 | 23.6 q | 1.02 s, 3H |
| 33 | 14.3 q | 0.87 d, 3H (7) |
| 34 | 16.9 q | 0.95 d, 3H (6.8) |
| 35 | 12.5 q | 1.74 s, 3H |
| 36 | 13.3 q | 1.72 m, 3H |
| 37 NH | | 7.75 m |
| 38 | 161.6 s | |
| 39 | 154.6 s | |
| 40 | 89.0 t | 5.07 d (1.6)<br>4.47 d (1.6) |
| 2-OH | | 4.75 d (5.6) |
| 4-O<u>C</u>ONH$_2$ | 156.7 s | |
| 4-OCON<u>H</u>$_2$ | | 6.35 br s, 2H |
| 13-OH | | 4.13 s |
| 20-OCH3 | 54.6 q | 3.24 s, 3H |
| 39-OCH3 | 55.5 q | 3.59 s, 3H |

EXAMPLE 2

Antitumor Effects of Raspailamide A (I) and B (II).

A. Effects of Raspailamide on Proliferation of Tumor Cell Lines

Raspailamide A (I) and B (II) were analyzed as to their effect on the proliferation of A549 human lung adenocarcinoma and P388 murine leukemia cell lines. P388 cells were obtained from Dr. R. Camalier, National Cancer Institute, Bethesda, Md., and A549 cells were obtained from American Type Culture Collection, Rockville, Md.

All cell lines are maintained in Roswell Park Memorial Institute (RPMI) medium 1640 supplemented with 100 U/mL penicillin 100 μg/ml streptomycin, 60 μg/ml L-glutamine, 18 mM HEPES, 0.05 mg/mL gentamycin and 10% fetal bovine serum. Cell lines are cultured in plastic tissue culture flasks and kept in an incubator at 37° C. in humidified air containing 5% $CO_2$.

To assess the antiproliferative effects of agents against the various cell lines, 200 μl cultures (96-well tissue culture plates, Nunc, Denmark) are first established at $3\times10^4$ cells/ml for adherent lines (A549) and 1×105 for non-adherent lines (P388) in tissue culture medium and incubated for 24 hr at 37° C. in 10% $CO_2$ in air in order to allow cells to attach. A volume of 100 μl of medium is removed from each test well and 100 μl of medium containing serial, two-fold dilutions of the test agent is added to each well containing tumor cells. Medium without drug is also added to wells containing tumor cells which serve as no drug controls. Positive drug controls are included to monitor drug sensitivity of each of the cell lines. These include varying dilutions of 5-fluorouracil, doxorubicin.

After 72-h exposures (Adherent cell lines) or 48-hr exposure (Non-adherent cell lines), tumor cells are enumerated using 3-[4,5-Dimethylthiazol-2-yl]-2,5-diphenyltetrazolium bromide (MTT) (M. C. Alley, et al., Cancer Res. 48:589, 1988) as follows:

A volume of 75 μl of warm growth media containing 5 mg/ml MTT is added to each well, cultures returned to the incubator, and left undisturbed for 3 hours. To spectrophotometrically quantitate formation of reduced formazan, plates are centrifuged (900×g, 5 minutes), culture fluids removed by aspiration, and 200 μl of acidified isopropanol (2 ml concentrated HCl/iter isopropanol) added per well. The absorbance of the resulting solutions is measured at 570 nm with a plate reader (Spectra II (Tecan Laboratories).

The absorbance of tests wells is divided by the absorbance of drug-free wells, and the concentration of agent that results in 50% of the absorbance of untreated cultures (IC50) is determined by linear regression of logit-transformed data (D. J. Finney, Statistical Method in Biological Assay, third ed., pp.316–348, Charles Griffin Co., London, 1978). A linear relationship between tumor cell number and formazan production has been routinely observed over the range of cell densities observed in these experiments.

The two standard drug controls (indicated above) are included in each assay to monitor the drug sensitivity of each of the cell lines and $IC_{50}$ values are determined for each drug-cell combination.

A summary of results in these assays for compounds I and II can be found in Table 2.

TABLE 2

Cytotoxicity Results for Raspailamides

| | A549 $IC_{50}$ | P388 $IC_{50}$ |
|---|---|---|
| Raspailamide A (I) | $4.6 \times 10^{-5}$ μg/mL | $4.0 \times 10^{-9}$ μg/mL |
| Raspailamide (II) | $1.8 \times 10^{-5}$ μg/mL | $6.7 \times 10^{-9}$ μg/mL |

EXAMPLE 3

Formulation and Administration

The compounds of the invention are useful for various non-therapeutic and therapeutic purposes. It is apparent from the testing that the compounds of the invention are effective for inhibiting cell growth. Because of the antiproliferative properties of the compounds, they are useful to prevent unwanted cell growth in a wide variety of settings including in vitro uses. They are also useful as standards and for teaching demonstrations. As disclosed herein, they are also useful prophylactically and therapeutically for treating cancer cells in animals and humans.

Therapeutic application of the new compounds and compositions containing them can be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the cancer cells, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as an active ingredient, an effective amount of one or more of the new compounds and one or more non-toxic, pharmaceutically acceptable carrier or diluent. Examples of such carriers for use in the invention include ethanol, dimethyl sulfoxide, glycerol, silica, alumina, starch, and equivalent carriers and diluents.

To provide for the administration of such dosages for the desired therapeutic treatment, new pharmaceutical compositions of the invention will advantageously comprise between about 0.1% and 45%, and especially, 1 and 15%, by weight of the total of one or more of the new compounds based on the weight of the total composition including carrier or diluent. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A compound having a structural formula selected from the group consisting of:

(I)

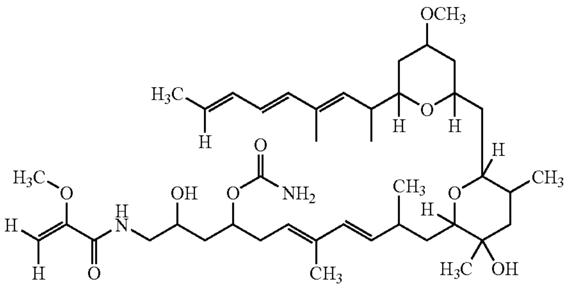

and

-continued (II)

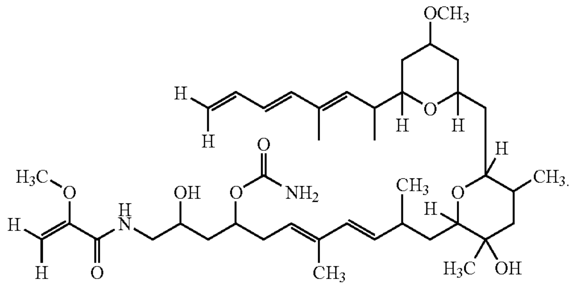

2. The compound, according to claim 1, having the following structure:

(I)

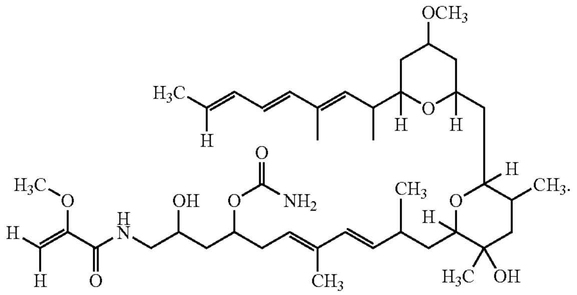

3. The compound, according to claim 1, having the following structure:

(II)

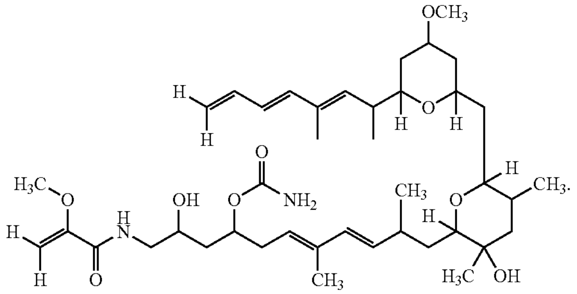

4. The compound, according to claim 1, having the following spectroscopic properties:

| Atom # | $^{13}C$ δ mult. | $^{1}H$ δ mult (J in Hz) |
|---|---|---|
| 1 | 45.5 t | 3.15 ddd |
| | | 3.00 ddd |
| 2 | 65.5 d | 3.57 m |
| 3 | 38.7 t | 1.50 dd |
| | | 1.37 dd |
| 4 | 70.0 d | 4.74 m |
| 5 | 33.4 t | 2.32 m, 2H |
| 6 | 124.9 d | 5.34 m |
| 7 | 135.3 s | — |
| 8 | 132.9 d | 5.97 d (16.1) |
| 9 | 133.6 d | 5.39 m |
| 10 | 33.5 d | 2.33 m |
| 11 | 35.7 t | 1.53 m |
| | | 1.20 m |
| 12 | 83.2 d | 2.92 m |
| 13 | 67.1 s | — |
| 14 | 47.0 t | 1.73 m |
| | | 1.55 m |
| 15 | 31.9 d | 1.73 m |
| 16 | 75.9 d | 3.39 m |
| 17 | 38.5 t | 1.67 ddd |
| | | 1.32 m |
| 18 | 72.4 d | 3.37 m |
| 19 | 37.0 t | 1.99 m |
| | | 0.91 m |
| 20 | 76.3 d | 3.26 m |
| 21 | 34.5 t | 1.95 m |
| | | 0.92 m |
| 22 | 78.6 d | 3.17 m |
| 23 | 37.1 d | 2.59 m |
| 24 | 135.5 d | 5.43 m |
| 25 | 133.4 s | — |
| 26 | 137.4 d | 6.23 d (15.3) |
| 27 | 121.6 d | 6.39 dd (15.3, 10.9) |
| 28 | 129.9 d | 6.03 m |
| 29 | 125.1 d | 5.44 dt |
| 30 | 12.6 q | 1.67 s, 3H |
| 31 | 22.1 q | 0.99 d, 3H (6.8) |
| 32 | 23.6 q | 1.02 s, 3H |
| 33 | 14.3 q | 0.87 d, 3H (7) |
| 34 | 16.9 q | 0.95 d, 3H (6.8) |
| 35 | 12.5 q | 1.74 s, 3H |
| 36 | 13.3 q | 1.72 m, 3H |
| 37 NH | | 7.75 m |
| 38 | 161.6 s | |
| 39 | 154.6 s | |
| 40 | 89.0 t | 5.07 d (1.6) |
| | | 4.47 d (1.6) |
| 2-OH | | 4.75 d (5.6) |
| 4-OCONH$_2$ | 156.7 s | |
| 4-OCONH$_2$ | | 6.35 br s, 2H |
| 13-OH | | 4.13 s |
| 20-OCH3 | 54.6 q | 3.24 s, 3H |
| 39-OCH3 | 55.5 q | 3.59 s, 3H. |

5. A method for inhibiting proliferation of lung cancer or leukemia cells, said method comprising administering to a patient in need of such treatment an effective amount of a compound having a structural formula selected from the group consisting of:

(I)

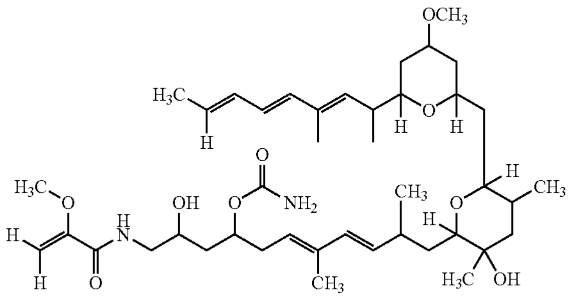

and

-continued (II)

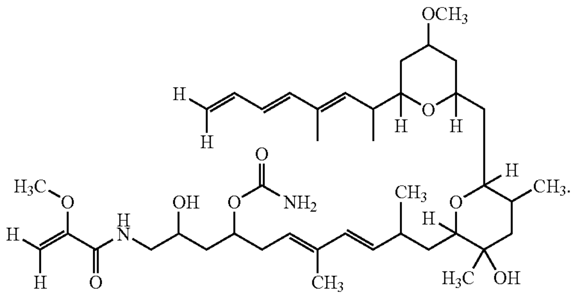

6. The method, according to claim 5, wherein the compound has the following structure:

(I)

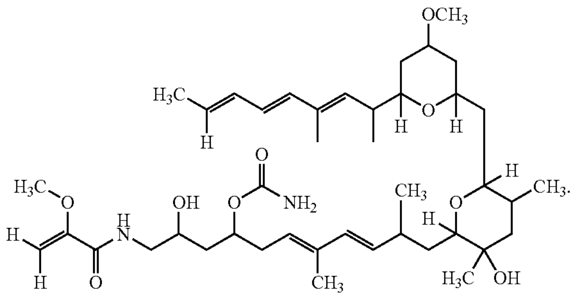

7. The method, according to claim 5, wherein the compound has the following structure:

(II)

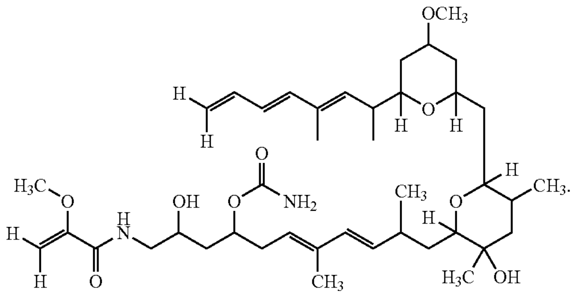

8. The method, according to claim 5, wherein said compound has the following spectroscopic properties:

| Atom # | $^{13}C$ δ mult. | $^{1}H$ δ mult (J in Hz) |
|---|---|---|
| 1 | 45.5 t | 3.15 ddd |
| | | 3.00 ddd |
| 2 | 65.5 d | 3.57 m |
| 3 | 38.7 t | 1.50 dd |
| | | 1.37 dd |
| 4 | 70.0 d | 4.74 m |
| 5 | 33.4 t | 2.32 m, 2H |
| 6 | 124.9 d | 5.34 m |
| 7 | 135.3 s | — |
| 8 | 132.9 d | 5.97 d (16.1) |
| 9 | 133.6 d | 5.39 m |
| 10 | 33.5 d | 2.33 m |
| 11 | 35.7 t | 1.53 m |
| | | 1.20 m |
| 12 | 83.2 d | 2.92 m |
| 13 | 67.1 s | — |
| 14 | 47.0 t | 1.73 m |
| | | 1.55 m |
| 15 | 31.9 d | 1.73 m |
| 16 | 75.9 d | 3.39 m |
| 17 | 38.5 t | 1.67 ddd |
| | | 1.32 m |
| 18 | 72.4 d | 3.37 m |
| 19 | 37.0 t | 1.99 m |
| | | 0.91 m |
| 20 | 76.3 d | 3.26 m |
| 21 | 34.5 t | 1.95 m |
| | | 0.92 m |
| 22 | 78.6 d | 3.17 m |
| 23 | 37.1 d | 2.59 m |
| 24 | 135.5 d | 5.43 m |
| 25 | 133.4 s | — |
| 26 | 137.4 d | 6.23 d (15.3) |
| 27 | 121.6 d | 6.39 dd (15.3, 10.9) |
| 28 | 129.9 d | 6.03 m |
| 29 | 125.1 d | 5.44 dt |
| 30 | 12.6 q | 1.67 s, 3H |
| 31 | 22.1 q | 0.99 d, 3H (6.8) |
| 32 | 23.6 q | 1.02 s, 3H |
| 33 | 14.3 q | 0.87 d, 3H (7) |
| 34 | 16.9 q | 0.95 d, 3H (6.8) |
| 35 | 12.5 q | 1.74 s, 3H |
| 36 | 13.3 q | 1.72 m, 3H |
| 37 NH | | 7.75 m |
| 38 | 161.6 s | |
| 39 | 154.6 s | |
| 40 | 89.0 t | 5.07 d (1.6) |
| | | 4.47 d (1.6) |
| 2-OH | | 4.75 d (5.6) |
| 4-O$\underline{C}$ONH$_2$ | 156.7 s | |
| 4-OCON$\underline{H_2}$ | | 6.35 br s, 2H |
| 13-OH | | 4.13 s |
| 20-OCH3 | 54.6 q | 3.24 s, 3H |
| 39-OCH3 | 55.5 q | 3.59 s, 3H. |

9. A pharmaceutical composition comprising a compound having a structural formula selected from the group consisting of:

(I)

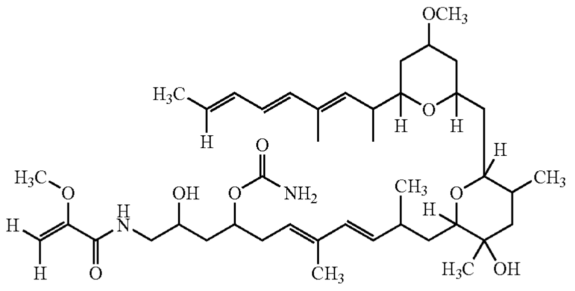

and

-continued (II)

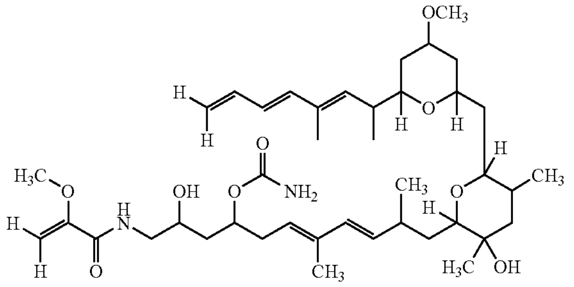

wherein said composition further comprises a pharmaceutically acceptable carrier.

10. The pharmaceutical composition, according to claim 9, comprising a compound having the following structure:

(I)

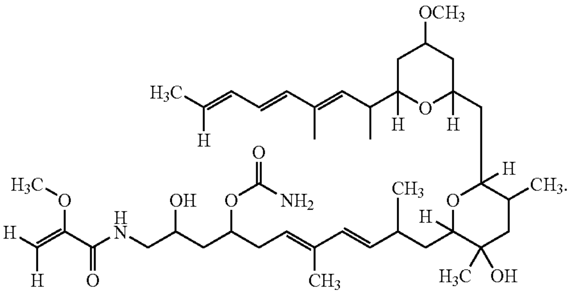

11. The pharmaceutical composition, according to claim 9, comprising a compound having the following structure:

(II)

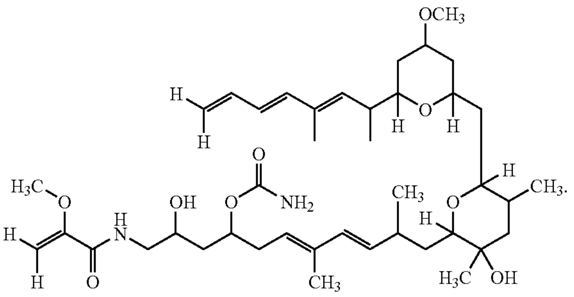

12. The composition, according to claim 9, comprising a compound having the following spectroscopic properties:

| Atom # | $^{13}C$ δ mult. | $^{1}H$ δ mult (J in Hz) |
|---|---|---|
| 1 | 45.5 t | 3.15 ddd |
| | | 3.00 ddd |
| 2 | 65.5 d | 3.57 m |
| 3 | 38.7 t | 1.50 dd |
| | | 1.37 dd |
| 4 | 70.0 d | 4.74 m |
| 5 | 33.4 t | 2.32 m, 2H |
| 6 | 124.9 d | 5.34 m |
| 7 | 135.3 s | — |
| 8 | 132.9 d | 5.97 d (16.1) |
| 9 | 133.6 d | 5.39 m |
| 10 | 33.5 d | 2.33 m |
| 11 | 35.7 t | 1.53 m |
| | | 1.20 m |
| 12 | 83.2 d | 2.92 m |
| 13 | 67.1 s | — |
| 14 | 47.0 t | 1.73 m |
| | | 1.55 m |
| 15 | 31.9 d | 1.73 m |
| 16 | 75.9 d | 3.39 m |
| 17 | 38.5 t | 1.67 ddd |
| | | 1.32 m |
| 18 | 72.4 d | 3.37 m |
| 19 | 37.0 t | 1.99 m |
| | | 0.91 m |
| 20 | 76.3 d | 3.26 m |
| 21 | 34.5 t | 1.95 m |
| | | 0.92 m |
| 22 | 78.6 d | 3.17 m |
| 23 | 37.1 d | 2.59 m |
| 24 | 135.5 d | 5.43 m |
| 25 | 133.4 s | — |
| 26 | 137.4 d | 6.23 d (15.3) |
| 27 | 121.6 d | 6.39 dd (15.3, 10.9) |
| 28 | 129.9 d | 6.03 m |
| 29 | 125.1 d | 5.44 dt |
| 30 | 12.6 q | 1.67 s, 3H |
| 31 | 22.1 q | 0.99 d, 3H (6.8) |
| 32 | 23.6 q | 1.02 s, 3H |
| 33 | 14.3 q | 0.87 d, 3H (7) |
| 34 | 16.9 q | 0.95 d, 3H (6.8) |
| 35 | 12.5 q | 1.74 s, 3H |
| 36 | 13.3 q | 1.72 m, 3H |
| 37 NH | | 7.75 m |
| 38 | 161.6 s | |
| 39 | 154.6 s | |
| 40 | 89.0 t | 5.07 d (1.6) |
| | | 4.47 d (1.6) |
| 2-OH | | 4.75 d (5.6) |
| 4-OCONH$_2$ | 156.7 s | |
| 4-OCONH$_2$ | | 6.35 br s, 2H |
| 13-OH | | 4.13 s |
| 20-OCH3 | 54.6 q | 3.24 s, 3H |
| 39-OCH3 | 55.5 q | 3.59 s, 3H. |

* * * * *

UNITED STATES PATENT AND TRADEMARK OFFICE

CERTIFICATE OF CORRECTION

PATENT NO. : 7,094,803 B2
APPLICATION NO. : 10/889925
DATED : August 22, 2006
INVENTOR(S) : Killday et al.

It is certified that error appears in the above-identified patent and that said Letters Patent is hereby corrected as shown below:

Column 8,
Line 3, "DBMR number 30-VEI-93-4-0 11" should read --DBMR number 30-VIII-93-4-0 11"

Column 10,
Line 65, "1 x 105 for non-adherent" should read --1 x $10^5$ for non-adherent--.

Column 11,
Line 20, "concentrated HCl/iter" should read --concentrated HCl/liter--.

Signed and Sealed this

Twentieth Day of March, 2007

JON W. DUDAS

*Director of the United States Patent and Trademark Office*